(12) United States Patent
Ganz et al.

(10) Patent No.: US 10,722,267 B2
(45) Date of Patent: Jul. 28, 2020

(54) BLOCKAGE REMOVAL

(71) Applicant: Piranha Medical, LLC, Salt Lake City, UT (US)

(72) Inventors: Robert A. Ganz, Minnetonka, MN (US); Mark Anders Rydell, Golden Valley, MN (US)

(73) Assignee: Piranha Medical, LLC, Salt Lake City, UT (US)

( * ) Notice: Subject to any disclaimer, the term of this patent is extended or adjusted under 35 U.S.C. 154(b) by 528 days.

(21) Appl. No.: 15/356,975

(22) Filed: Nov. 21, 2016

(65) Prior Publication Data

US 2017/0150993 A1 Jun. 1, 2017

Related U.S. Application Data

(60) Provisional application No. 62/260,873, filed on Nov. 30, 2015.

(51) Int. Cl.
*A61B 17/50* (2006.01)
*A61B 17/22* (2006.01)
*A61B 17/00* (2006.01)
*A61B 17/3205* (2006.01)

(52) U.S. Cl.
CPC .............. *A61B 17/50* (2013.01); *A61B 17/22* (2013.01); *A61B 17/32053* (2013.01); *A61B 2017/00818* (2013.01); *A61B 2017/22079* (2013.01); *A61B 2217/005* (2013.01); *A61B 2218/007* (2013.01)

(58) Field of Classification Search
CPC ................ A61B 17/1637; A61B 17/22; A61B 17/22012; A61B 17/22031; A61B 17/22035; A61B 17/32053; A61B 17/3207; A61B 17/320758; A61B 17/50; A61B 2017/00818; A61B 2017/22079; A61B 2017/320775; A61B 2017/320791; A61M 25/0021; A61M 25/0023; A61M 25/0082
See application file for complete search history.

(56) References Cited

U.S. PATENT DOCUMENTS

| 4,715,848 A | 12/1987 | Beroza |
| 4,754,755 A | 7/1988 | Husted |
| 4,772,258 A | 9/1988 | Marangoni et al. |
| 4,898,575 A | 2/1990 | Fischell et al. |

(Continued)

FOREIGN PATENT DOCUMENTS

| CN | 201642262 U | 11/2010 |
| KR | 100834042 B1 | 5/2008 |

(Continued)

OTHER PUBLICATIONS

Chen et al., "Esophageal Food impaction: A Homemade Suction Tube Attached to Esophagogastroduodenoscopy for Food Bolus Removal," Chin Med Assoc, Dec. 2008, vol. 71, No. 12, 5 pages.

(Continued)

*Primary Examiner* — Robert A Lynch
(74) *Attorney, Agent, or Firm* — Med Venture Management, LLC; Daniel C. Higgs (57) ABSTRACT

A device is configured to clear a bolus of food impacted within an esophagus, the device including a catheter tube having a hollow interior and a distal end configured to core the bolus of food and a proximal end configured to be coupled to a source of suction to clear the core.

22 Claims, 11 Drawing Sheets

(56) References Cited

U.S. PATENT DOCUMENTS

| | | | |
|---|---|---|---|
| 5,033,466 A | | 7/1991 | Weymuller, Jr. |
| 5,114,399 A | | 5/1992 | Kovalcheck et al. |
| 5,197,949 A | | 3/1993 | Angsupanich |
| 5,695,448 A | | 12/1997 | Kimura et al. |
| 5,741,269 A | | 4/1998 | McCredy |
| 5,782,837 A | | 7/1998 | York |
| 5,921,971 A | | 7/1999 | Agro et al. |
| 5,931,831 A | | 8/1999 | Linder et al. |
| 6,042,593 A | * | 3/2000 | Storz ............... A61B 17/32002 606/159 |
| 6,361,540 B1 | | 3/2002 | Gauderer et al. |
| 6,689,062 B1 | | 2/2004 | Mesallum |
| 6,699,260 B2 | | 3/2004 | Dubrul et al. |
| 6,840,909 B2 | | 1/2005 | Gatto |
| 6,971,988 B2 | | 12/2005 | Orban, III |
| 6,986,773 B1 | | 1/2006 | Manougian |
| 7,204,804 B2 | | 4/2007 | Zirps et al. |
| 7,220,253 B2 | | 5/2007 | Kantsevoy et al. |
| 7,727,186 B2 | | 6/2010 | Makower et al. |
| 8,016,785 B2 | | 9/2011 | Kantsevoy et al. |
| 8,016,838 B2 | | 9/2011 | Kaye et al. |
| 8,057,484 B2 | | 11/2011 | Secrest et al. |
| 8,377,075 B2 | | 2/2013 | Lichtenstein et al. |
| 8,573,218 B2 | | 11/2013 | Rutter |
| 8,591,521 B2 | | 11/2013 | Cherry et al. |
| 8,602,974 B2 | | 12/2013 | Goldwasser et al. |
| 8,852,219 B2 | | 10/2014 | Wulfman et al. |
| 8,870,824 B2 | | 10/2014 | Kusakabe |
| 8,876,838 B2 | | 11/2014 | Winiarski |
| 8,906,169 B2 | | 12/2014 | Bagwell et al. |
| 9,549,761 B2 | | 1/2017 | Green et al. |
| 2005/0240147 A1 | | 10/2005 | Makower et al. |
| 2006/0074478 A1 | | 4/2006 | Feller, III |
| 2006/0293612 A1 | | 12/2006 | Jenson et al. |
| 2007/0208252 A1 | * | 9/2007 | Makower ............ A61B 5/6851 600/424 |
| 2007/0250149 A1 | * | 10/2007 | Von Oepen ............ A61F 2/958 623/1.11 |
| 2008/0103410 A1 | | 5/2008 | Karpiel et al. |
| 2008/0103508 A1 | | 5/2008 | Karakurum |
| 2008/0119693 A1 | | 5/2008 | Makower et al. |
| 2008/0188868 A1 | | 8/2008 | Weitzner et al. |
| 2008/0243137 A1 | * | 10/2008 | D'Angelo ........ A61B 17/32075 606/106 |
| 2009/0187098 A1 | | 7/2009 | Makower et al. |
| 2010/0016885 A1 | | 1/2010 | Eidenschink et al. |
| 2011/0275990 A1 | | 11/2011 | Besser et al. |
| 2011/0282353 A1 | | 11/2011 | McHugo |
| 2012/0071856 A1 | | 3/2012 | Goldfarb et al. |
| 2013/0103063 A1 | * | 4/2013 | Escudero ......... A61B 17/32075 606/159 |
| 2014/0052114 A1 | | 2/2014 | Ben-Oren et al. |
| 2014/0150782 A1 | * | 6/2014 | Vazales ............ A61M 16/0463 128/202.16 |
| 2014/0309673 A1 | * | 10/2014 | Dacuycuy ............ A61B 17/221 606/159 |
| 2015/0025558 A1 | | 1/2015 | Wulfman et al. |
| 2015/0057517 A1 | | 2/2015 | Pease et al. |
| 2016/0081702 A1 | | 3/2016 | Kan et al. |
| 2016/0262722 A1 | | 9/2016 | Marmor et al. |
| 2016/0331645 A1 | | 11/2016 | Bagwell et al. |
| 2016/0374700 A1 | | 12/2016 | Olden et al. |
| 2018/0280040 A1 | | 10/2018 | Ganz et al. |
| 2018/0344993 A1 | | 12/2018 | Ganz et al. |

FOREIGN PATENT DOCUMENTS

| | | |
|---|---|---|
| WO | 2008042987 A2 | 4/2008 |
| WO | 2008121292 A1 | 10/2008 |
| WO | 2017095682 A1 | 6/2017 |
| WO | 2018222948 A1 | 12/2018 |

OTHER PUBLICATIONS

Ho et al., "Review of food bolus management," http://www.ncbi.nlm.nih.gov/pmc/articles/PMC2661297/, Review of food bolus management, Can J Gastroenterol. Oct. 2008; 22(10): 805-808.

International Search Report and Written Opinion in PCT/US2016/063083 dated Feb. 22, 2017, 15 pages.

American Society for Gastrointestinal Endoscopy, Management of Ingested Foreign Bodies and Food Impactions, Gastrointestinal Endoscopy Journal, 2011, pp. 1085-1091, vol. 73, No. 6.

Benjamin, Esophageal Foreign Bodies and Food Impactions, Gastroenterology & Hepatology, Aug. 2008, pp. 546-548, vol. 4, Issue 8.

Birk et al., Removal of Foreign Bodies in the Upper Gastrointestinal Tract in Adults: European Society of Gastrointestinal Ensdoscopy (ESGE) Clinical Guideline, Endoscopy 2016, 2016, pp. 1-8.

Hobbs Medical, Inc., Aspiration Catheters, May 22, 2013, http://www.hobbsmedical.com/endoscopy-products-catheters-aspiration-catheter (archived at https://web.archive.org/web/20130522065728/http://www.hobbsmedical.com/endoscopy-products-catheters-aspiration-catheter.htm).

Hobbs Medical, Inc., Aspiration Catheters, Jun. 6, 2019, https://www.hobbsmedical.com/products/aspiration-catheters.

Kragha, Complete Gastroesophageal Obstruction by Food Bolus, Applied Radiology, Sep. 2016, pp. 40-44.

Shafique et al., New and Safe Treatment of Food Impacted in the Esophagus: A Single Center Experience of 100 Consecutive Cases, Gastroenterology Research and Practice, 2013, pp. 1-4, Hindawi Publishing Corporation, Article ID 142703.

International Searching Authority, International Search Report and Written Opinion of the International Searching Authority in International Application No. PCT/US2018/035507, dated Jul. 31, 2018, 8 pages.

U.S. Appl. No. 15/995,105, filed May 31, 2018, Blockage Clearing Devices, Systems, and Methods.

U.S. Appl. No. 15/995,112, filed May 31, 2018, Blockage Clearing Devices, Systems, and Methods.

International Application No. PCT/US2019/059475, filed Nov. 1, 2019, 153 pages.

International Searching Authority, International Search Report and Written Opinion of the International Searching Authority in International Application No. PCT/2019/059475, dated Jan. 14, 2020, 10 pages.

United States Patent and Trademark Office, Office Action for U.S. Appl. No. 15/995,112, dated Jan. 30, 2020, 28 pages.

United States Patent and Trademark Office, Office Action for U.S. Appl. No. 15/995,105, dated Feb. 6, 2020, 6 pages.

European Patent Office, Communication Pursuant to Article 94(3) EPC in European Patent Application No. 16810172.3, dated Mar. 20, 2020, 5 pages.

* cited by examiner

BLOCKAGE REMOVAL

BACKGROUND

Blockages within the body can take various forms. For example, esophageal food impactions are one of the most common and dangerous emergencies in gastroenterology, with an annual incidence rate of at least 13/100,000 population (Longstreth, GIE; 2001); moreover, the incidence has been increasing in recent years due to the recent rise in eosinophilic esophagitis (Desai, GIE; 2005). Food impactions can occur when a bolus of swallowed food becomes lodged in the esophagus and is unable to pass spontaneously into the stomach. This occurs either when the swallowed bolus is too large or when there are diseases of the esophagus that narrow the esophageal lumen, such as GE reflux with a stricture or ring, an esophageal food allergy such as eosinophilic esophagitis with stricture or stenosis of the esophagus, a Schatzki's ring, esophageal webs or esophageal cancer. Motility disorders of the esophagus typically do not cause impactions.

Most impactions clear spontaneously, but a significant fraction (20%) will not and will require emergent endoscopic intervention to clear the blocked food. This can be dangerous, since emergency endoscopy with removal of food can result in serious complications including aspiration pneumonia, laceration of the esophagus with bleeding, or esophageal perforation which can result in sepsis and death. The complication rate of endoscopic clearance of a food impaction is approximately 3-5% and the mortality rate is unknown but several deaths have been reported (Simic, Am J Forensic Med Path; 198).

Food impactions present acutely and dramatically, with patients noting chest pain or pressure, inability to swallow, painful swallowing, a sensation of choking, and neck or throat pain. Retching and vomiting are also common, and patients can also experience breathing problems due to tracheal or airway compression, with stridor, coughing or wheezing being noted.

There are various endoscopic tools used to clear impactions but all have flaws and there is no current technique that is demonstrably better than any other. Food can sometimes be pushed blindly through the esophagus and into the stomach using the tip of the endoscope, but this technique is performed without vision of the more distal esophagus, so the endoscopist has no way of knowing what the esophagus looks like distal to the obstruction or what abnormalities exist. This technique can work well (Vicari, GIE; 2001), but because the technique is blind, can often result in esophageal laceration or perforation. Many endoscopists avoid blind pushing for this reason. Forceps including "rat-tooth" type designs, snares and variable wire basket designs can be used to break up food into smaller pieces for extraction, but these techniques are laborious, time-consuming and often fail.

Other extraction techniques can also be tried, particularly when the food bolus is not tightly wedged and is firm, or if the food contains bone or sharp surfaces. In this regard, baskets, snares, graspers, "pelican" forceps with longer arms, nets etc., can be used to remove food in whole or in pieces, but these techniques also frequently fail, and the patient is at risk for aspiration pneumonia if the pieces fall into the hypopharynx or mouth during the extraction attempts. If the food bolus is lodged proximally, then most of the above techniques will fail or are too dangerous to try. Endoscopic suction cannot be used for impactions, since chunks of food cannot be effectively suctioned through an endoscope, and also if suction fails to hold a bolus against the tip of the scope then a patient would be at high-risk for aspiration as the scope is withdrawn through the hypopharynx or mouth. Overtubes can be used if repeated endoscopic intubation is needed, but overtubes are uncomfortable, require deeper sedation and are dangerous in of themselves with risk of esophageal laceration and perforation.

Thus, it is important to provide mechanisms to clear blockages within the body. For example, within the field of esophageal food impaction, there is a need for effective and safer mechanisms to remove food stuck in the esophagus.

SUMMARY

Systems and methods are provided to address blockages within the body.

In one example, a device is configured to clear a bolus of food impacted within an esophagus, the device including a catheter tube having a hollow interior and a distal end configured to core the bolus of food and a proximal end configured to be coupled to a source of suction to clear the core.

DETAILED DESCRIPTION

Example devices and methods described herein address the removal of blockages within the body. Although some of the examples depicted herein relate to the removal of impactions within the esophagus, the inventions are not so limited. For example, the inventions described herein can also be used to remove or otherwise break-up other blockages within the body, such as those in the lungs.

Some of the systems described herein assist in resolving the buildup of pieces of food in the esophagus while minimizing the risk of aspiration. The systems are further designed in an atraumatic manner, helping to avoid esophageal laceration and perforation. One such approach consistent with the embodiments disclosed involves coring out the center of a food impaction.

For example, in one embodiment, the system includes a catheter (e.g., hollow) with a distal end that is delivered to the site of the blockage. The distal end is used to core out portions of the blockage until the blockage is reduced in volume in a piecemeal manner. The smaller volume blockage can then pass through the esophagus spontaneously and/or be more easily removed. In some examples, the catheter can be delivered to the blockage site through an endoscope or other similar device.

In certain examples, suction can be provided to remove the cored portions of the blockage. The suction can be provided at the proximal end of the catheter to cause the cored portions to be suctioned from the site of the blockage and passed through the catheter and discarded, thus minimizing a risk of food aspiration and preserving visualization.

Certain embodiments include aspects that allow cored portions of the food to be cleared should the portions become caught in the catheter while being suctioned away from the blockage site. In one example, a source of compressed air, such as a syringe, can be placed at the proximal end of the catheter, and air can be passed through the catheter to clear any portions caught in the catheter, via the distal end.

In addition, a stylet can be passed through the interior of the catheter to clear any portions of food caught therein. The stylet can also perform other functions, such as providing stiffness for the catheter during delivery of the catheter to the blockage site. Further, the stylet can be configured to assist in the manipulation of the blockage, such as by advancing the stylet into the blockage one or multiple times to create a nidus for coring and suctioning.

Figure 1:
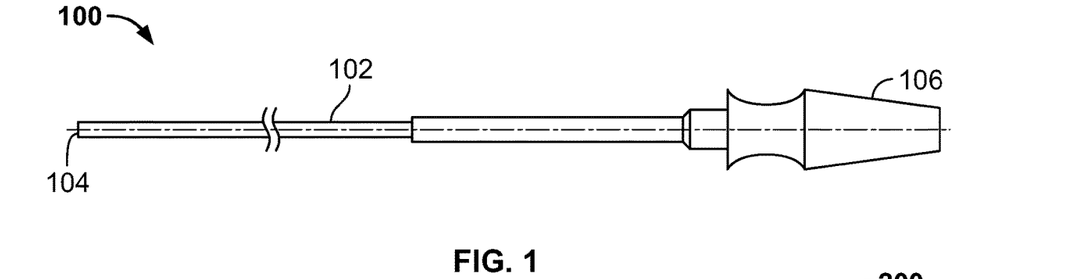
FIG. 1 shows an example catheter for removing a blockage within a body of a person.

Referring now to FIG. 1, an example catheter 100 is shown. The catheter 100 includes a hollow catheter tube 102 that generally can be used to core out a portion of a blockage. Specifically, the catheter tube 102 includes a distal end 104 that is configured to contact and core the blockage one or more times. As the blockage is cored by the distal end 104 of the catheter tube 102, the volume of the blockage is reduced until the blockage is reduced to a sufficient level to be passed through the esophagus spontaneously and/or removed.

The catheter tube 102 includes a proximal end 106 configured to be coupled to various devices. For example, as described further below, the proximal end 106 of the catheter tube 102 is configured to be coupled to a source of suction to allow the cored food portions to be suctioned and/or removed through the catheter tube 102. In another example, the proximal end 106 of the catheter tube 102 is configured to be coupled to a source of pressurized air, such as a syringe, to allow any cored food stuck within the catheter tube 102 to be cleared. Other configurations are possible.

Figure 2:
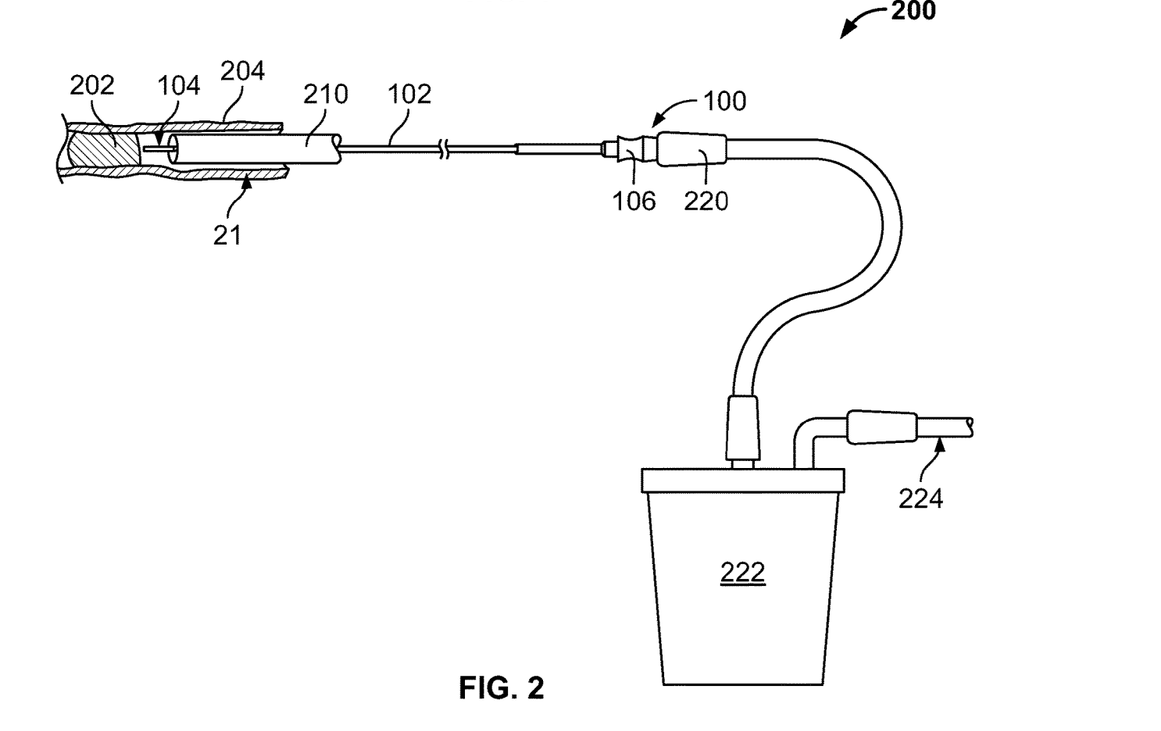
FIG. 2 shows an example system for removing a bolus of food or other debris lodged within an esophagus including the catheter of FIG. 1.
Figure 3:
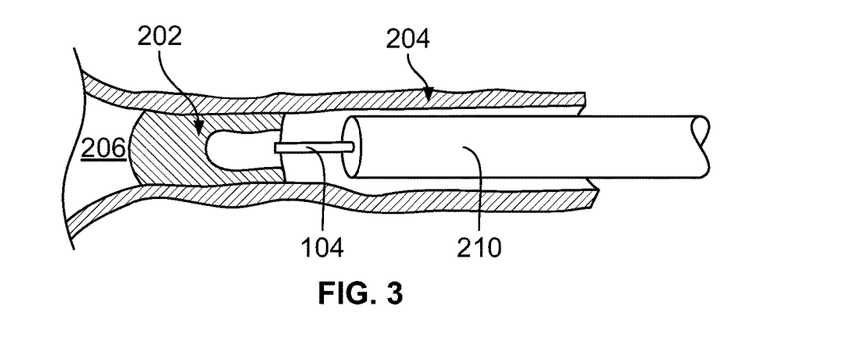
FIG. 3 shows a portion of the system of FIG. 2 with the bolus of food or other debris being partially cored.

Referring now to FIGS. 2-3, the catheter 100 is shown within an example system 200 configured to remove a blockage 202 positioned within an esophagus 204 of a person. In this example, the blockage 202 (generally food or other debris, but could also be other blockages like blood or blood clots, mucus, etc.) has become caught within the esophagus 204.

In the embodiment shown, the catheter 100 is delivered to the blockage 202 using an endoscope 210. The endoscope 210 contains a channel that is generally hollow and allows the catheter 100 to be delivered through the endoscope 210 to the blockage 202. Once the distal end 104 of the catheter tube 102 is in position, the endoscope 210 can be withdrawn or can remain in place as the blockage 202 is manipulated.

The catheter tube 102 of the catheter 100 is configured to be advanced so that the distal end 104 impacts the blockage 202 so as to reduce the volume of the blockage 202, such as by repetitively coring the food. As the volume is reduced (such as is shown in FIG. 3), the blockage 202 can be naturally passed through the esophagus 204 and into a stomach 206 of the person.

In example embodiments, the catheter tube 102 is at least semi-rigid but flexible, which allows the catheter tube to flex and/or bend during delivery through the endoscope, as the endoscope flexes and bends. This allows the catheter tube 102 to be directed more precisely as it is inserted to a desired location.

Figure 4:
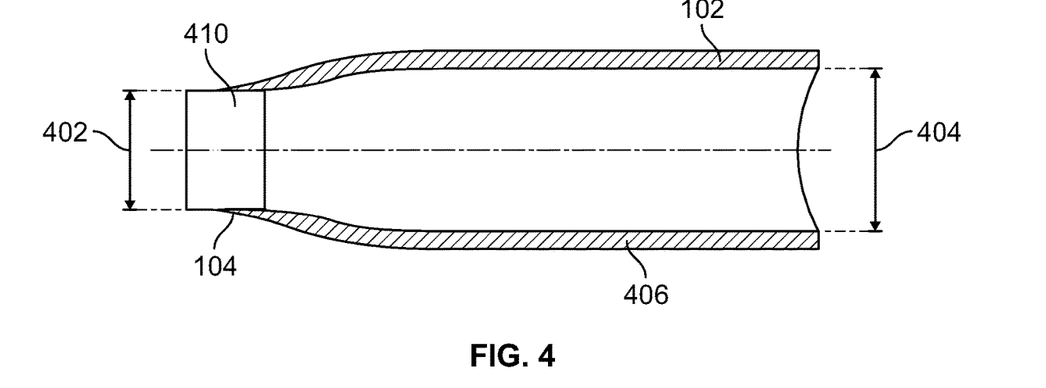
FIG. 4 shows an example distal end of the catheter for coring the bolus of food or other debris shown in FIG. 1.

In some examples, the distal end 104 of the catheter tube 102 is configured to assist in the coring of the blockage 202. For example, as shown in FIG. 4, the distal end 104 of the catheter tube 102 is tapered. Specifically, the distal end 104 includes an inner diameter 402 that is smaller than an inner diameter 404 of a portion 406 of the catheter tube 102. In one example, the difference in diameters can be less than one-hundredth of a millimeter. Other sizes are possible. In addition, the walls of the catheter tube 102 can be thinned as the walls extend to the distal end 104, as depicted.

This tapering of the distal end 104 can allow a core 410 of the blockage 202 that is formed by the distal end 104 to be more easily suctioned through the catheter tube 102. Since the cores formed by the distal end 104 will typically have a diameter smaller than that of the portion 406, the cores can be more easily suctioned through the catheter tube 102 for evacuation, as is illustrated by Poiseuille's law.

Figure 5:
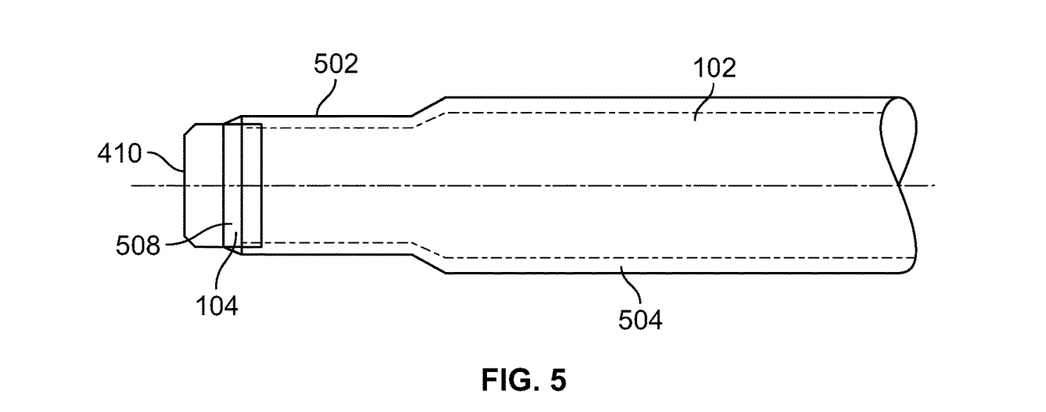
FIG. 5 shows another example distal end of the catheter for coring the bolus of food or other debris shown in FIG. 1.

In another depiction shown in FIG. 5, the catheter tube 102 is formed of a first portion 502 at the distal end 104 having a smaller diameter, and a second portion 504 extending along a remainder of the catheter tube 102 having a larger diameter. This again allows the cores of the blockage 202 that are created by the first portion 502 to be smaller in diameter so that the cores can more easily pass through the remainder of the catheter tube 102 (i.e., the second portion 504).

In some examples, a tip 508 of the distal end 104 of the catheter tube 102 can be beveled and/or serrated. The tip 508 can take multiple forms, including a serrated edge, to shave bits of the blockage 202 off of the bolus to better aid suctioning. The tip 508 can help core the blockage.

For example, referring again to the system 200 depicted in FIG. 2, a source of suction can be applied to the proximal end 106 of the catheter 100 to allow the cores of the blockage 202 to be removed through the catheter tube 102. Specifically, in the example provided, a vacuum line 220 can be coupled to the proximal end 106 of the catheter tube 102. The vacuum line 220 can be coupled to a collection canister 222, and the collection canister 222 is coupled to a suction line 224. The suction line 224 is coupled to a source of suction, such as a hospital vacuum source. In this configuration, pieces of the blockage 202 that are cored or otherwise dislodged by the catheter tube 102 can thereupon be sucked up the catheter tube 102, through the vacuum line 220, and collected in the collection canister 222.

As described previously, it is possible for one or more cores of the blockage 202 to become stuck within the catheter tube 102. In such a scenario, various devices can be used to clear the stuck cores.

Figure 6:
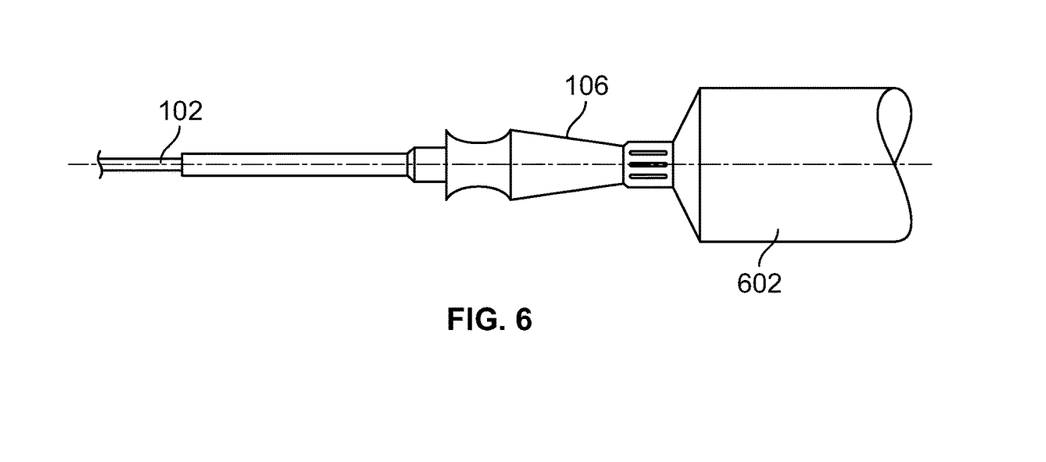
FIG. 6 shows a portion of an example catheter tube of FIG. 1 coupled to a syringe.

For example, referring now to FIG. 6, an example syringe 602 is coupled to the proximal end 106 of the catheter 100 using, for example, a suction line fitting or Luer-lock style connection. In this embodiment, the syringe 602 can be a typical 60 cc syringe that is used to deliver air into the catheter tube 102 during coring of the blockage 202 to dislodge and/or remove portions of the blockage 202 that are in the catheter tube 102.

In this instance, a plunger of the syringe 602 is actuated to displace air within the syringe 602 into and through the catheter tube 102. This air can be used to dislodge obstructions within the tube. Other configurations are possible. For example, other types of fluids, such as a jet spray of water, could be used to help clear the tube or break up food.

In other instances, different devices can be used to clear the catheter 100. For example, referring now to FIGS. 7-8, a stylet 700 is shown that is sized to fit through the hollow interior of the catheter tube 102. Generally, the stylet 700 can be used to perform various functions.

Figure 7:
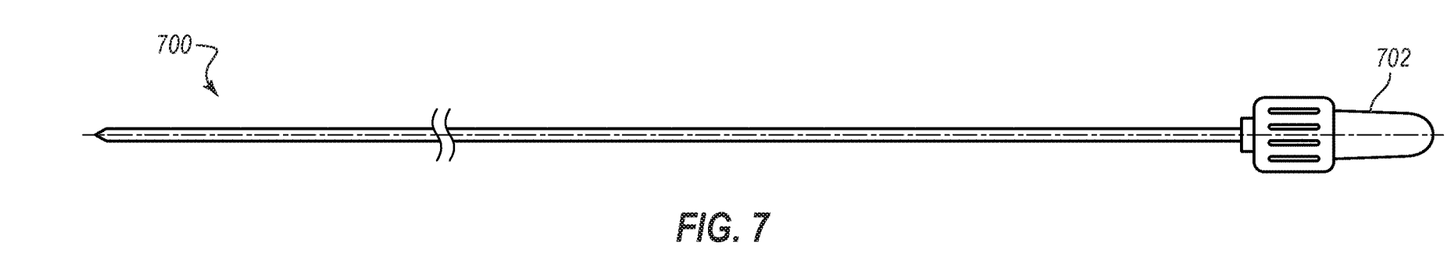
FIG. 7 shows an example stylet of the system of FIG. 2.
Figure 8:
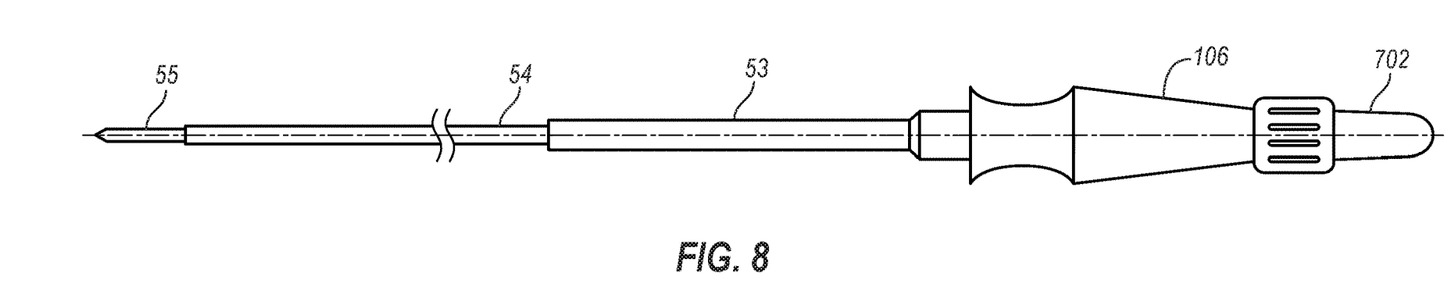
FIG. 8 shows the stylet of FIG. 7 positioned with the catheter of FIG. 1.

For example, the stylet 700 can be used to stiffen the catheter 100 during delivery to the blockage 202. Further, the stylet 700 can be introduced through the catheter tube 102 to clear the catheter tube 102 when one or more cores get stuck, performing a function of a pusher rod. Finally, the stylet 700 can also be used to pierce the blockage 202 to start a nidus for coring and suctioning. In some examples, the stylet 700 can also be solid or hollow.

In this example, the stylet 700 further includes a stylet knob 702 that is configured to be engaged with the proximal end 106 of the catheter 100. The proximal end 106 can be configured to include a Luer taper that allows the proximal end 106 to engage the stylet knob 702 of the stylet 700. Other coupling arrangements, such as a threaded engagement, can be used.

As shown in FIG. 8, the stylet knob 702 is coupled to the proximal end 106 of the catheter tube 102. In this configuration, the catheter 100 can be delivered to the desired location within the esophagus 204. At that time, the stylet knob 702 can be disengaged from the proximal end 106 to free the stylet 700 for movement. This movement can include the caregiver pushing the stylet 700 into and out of the catheter tube 102 to generally disrupt the blockage 202 and/or removal of the stylet 700 completely from the catheter tube 102.

When the stylet 700 is removed from the catheter tube 102, the vacuum line 220 can be connected to the proximal end 106 of the catheter tube 102 for suctioning, as described previously.

In this example shown in FIG. 8, the catheter tube 102 is approximately 80.5 inches in length and the stylet 700 is approximately 84 inches in length, although many different lengths can be provided such as, for example, shorter lengths for children and longer lengths for adults or to accommodate different length endoscopes, bronchoscopes or colonoscopes. The example catheter tube 102 has an outer diameter of 0.135 inches and an inner diameter of 0.115 inches. The stylet 700 has an outer diameter of 0.105 inches. Other sizes can be used.

In other embodiments, the catheter tube 102 can be variable in length and diameter. For example, another embodiment of the catheter tube 102 measures 0.093 inches in outer diameter and 0.082 for the inner diameter, allowing for easy introduction and sliding within the working channel of any endoscope. The catheter tube 102 is long enough to extend through an endoscope, at least 120 cm in length but can be longer.

The stylet 700 can vary in diameter, but in the preferred embodiment measures 0.070 inches in outer diameter to allow easy introduction and sliding within the catheter tube 102, and is slightly longer than the catheter tube 102 to allow the stylet 700 to extend beyond the distal end 104 of the catheter tube 102 to clear the catheter tube 102 and extend further into the blockage 202, if necessary.

The catheter tube 102 can be made from a thin-walled extruded tube sized to fit the working channel (biopsy channel) of any commercially available endoscope. One example material is Pebax 7233 SA. Another possible material would be an extrusion grade of PETG. Other possibilities would be Polyamide or extrusion grade Nylon or Delrin, such as Nylon 10 or Nylon 12.

The stylet 700 could be made of the same or similar material. For example, the catheter tube 102 and the stylet 700 can be made of the same material to allow the stylet 700 to fit within the catheter tube 102 while minimizing friction. However, other materials and different materials for each can be used.

The above materials would clear food, but would not seriously damage the walls of the esophagus should they inadvertently contact the walls of the esophagus.

Referring now to FIGS. 9-17, another example device 900 is shown. The device 900 includes the catheter tube 102 with a suction port 902 at the proximal end 106 and with the distal end 104 that is designed (e.g., beveled) to be advanced through the biopsy channel of any commercial endoscope and that can accommodate the stylet 700 to clear food that sticks in the catheter tube 102 after removal from the esophagus.

Figure 9:
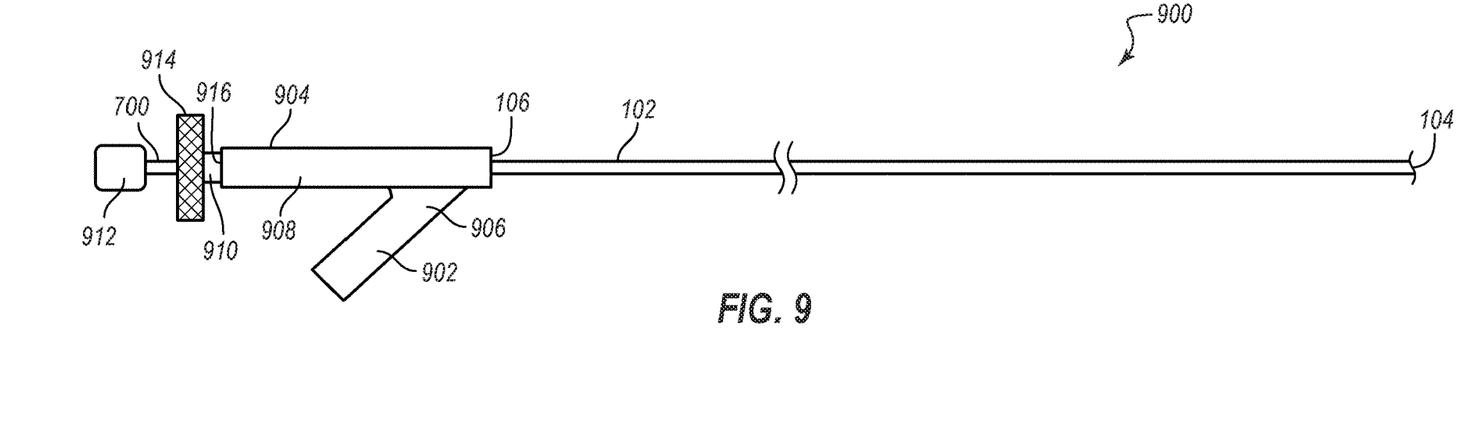
FIG. 9 shows another example catheter having a Y-fitting for removing a bolus of food or other debris lodged within an esophagus.
Figure 10:
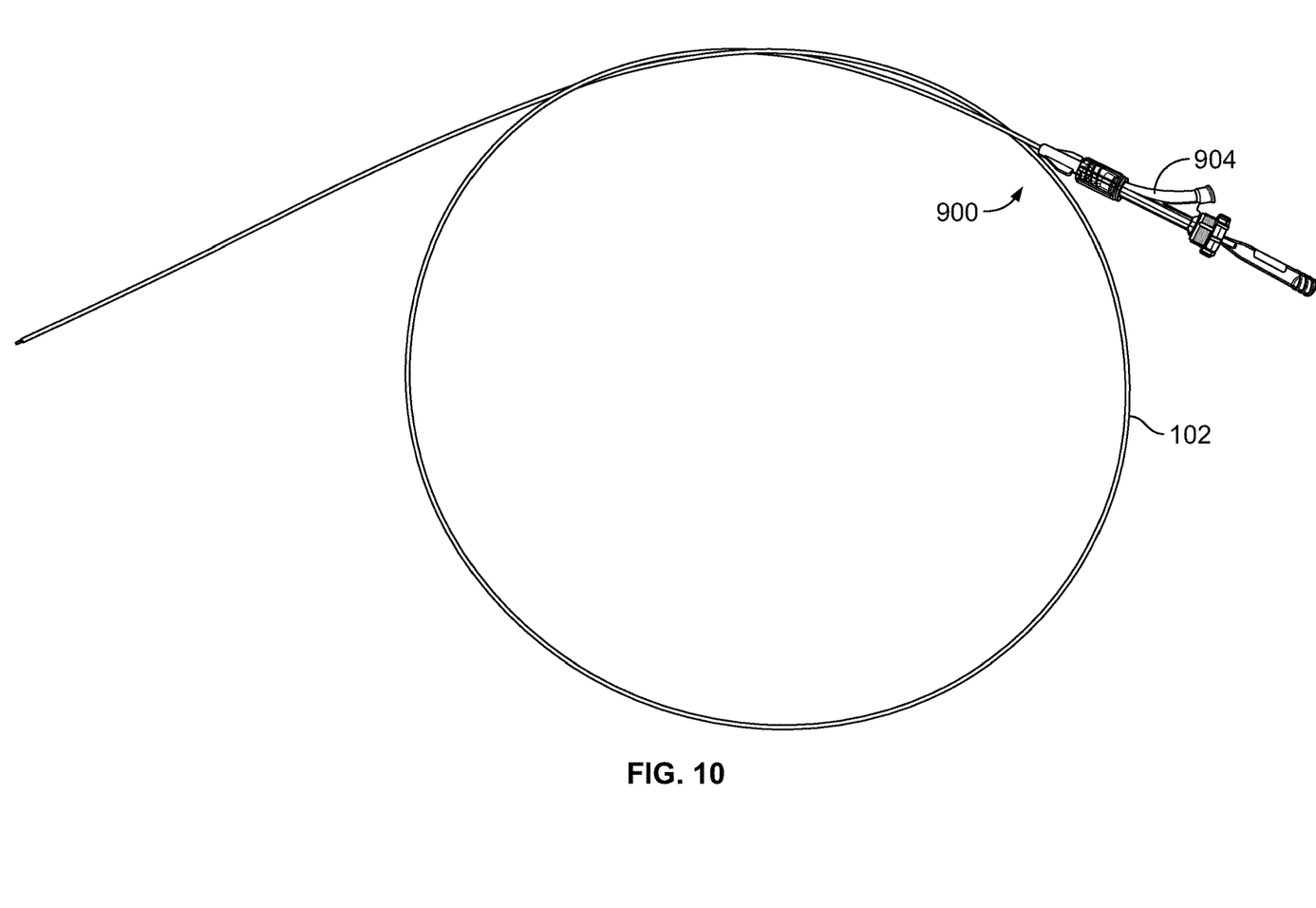
FIG. 10 shows another view of the catheter of FIG. 9.
Figure 11:
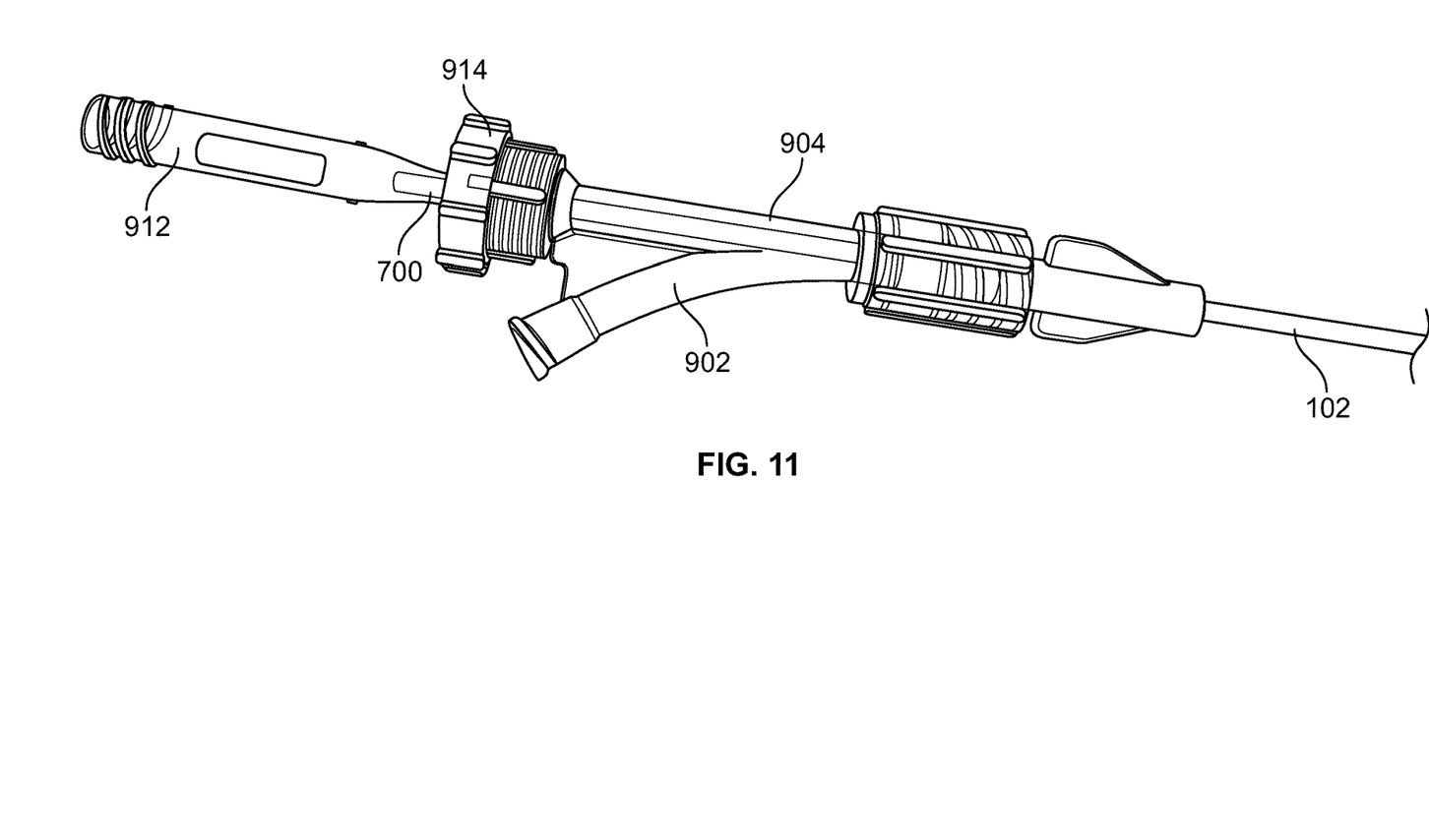
FIG. 11 shows a proximal portion of the catheter of FIG. 9 with a stylet advanced fully therethrough.
Figure 12:
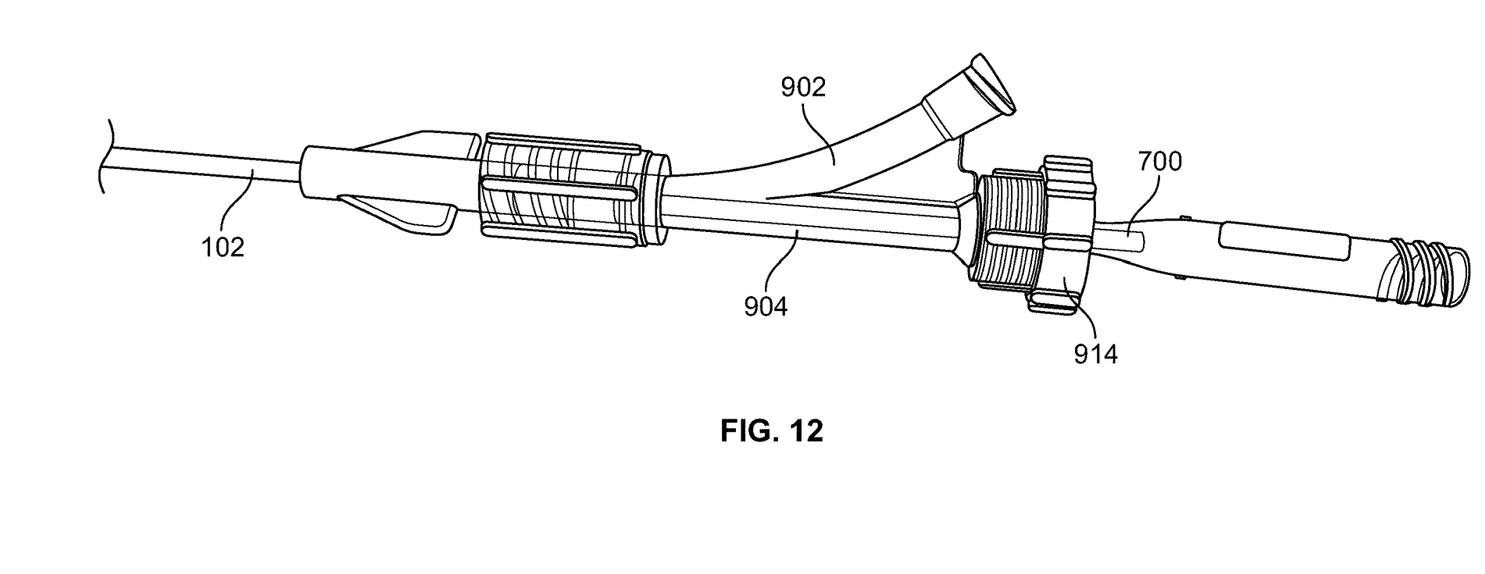
FIG. 12 shows another view of the proximal portion of the catheter of FIG. 11.
Figure 13:
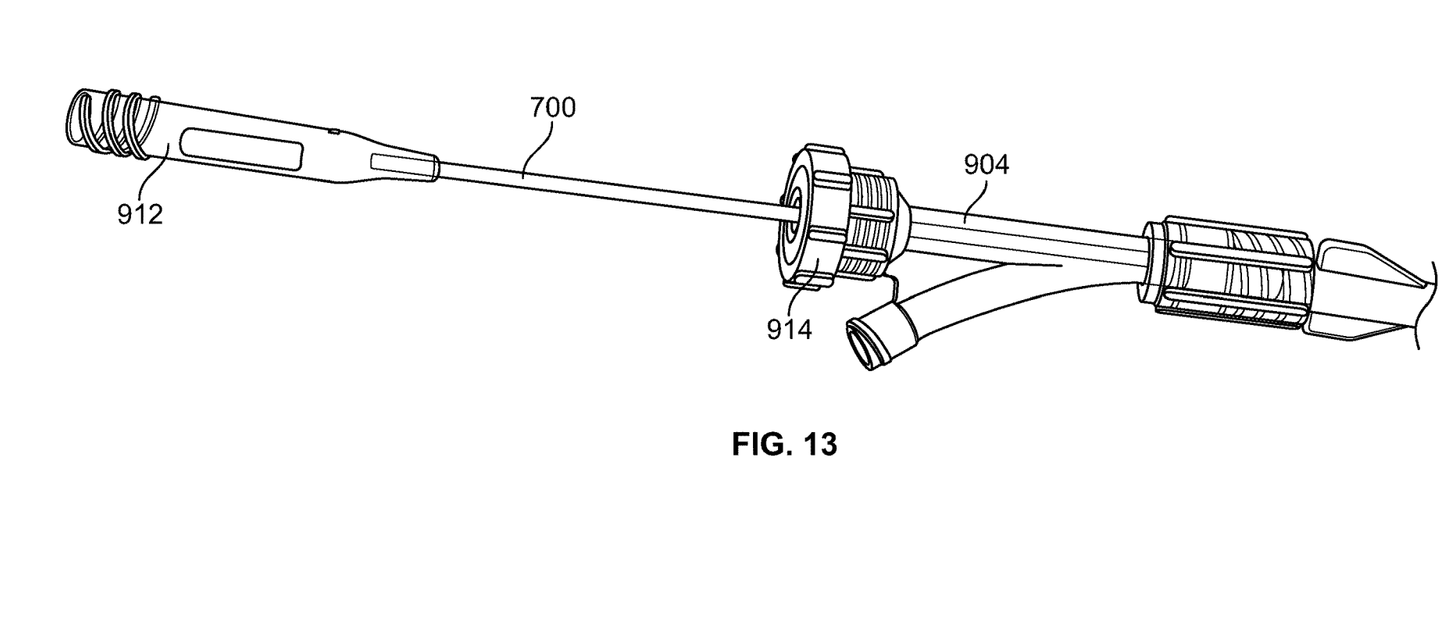
FIG. 13 shows another view of the proximal portion of the catheter of FIG. 11 with the stylet partially removed therefrom.
Figure 14:
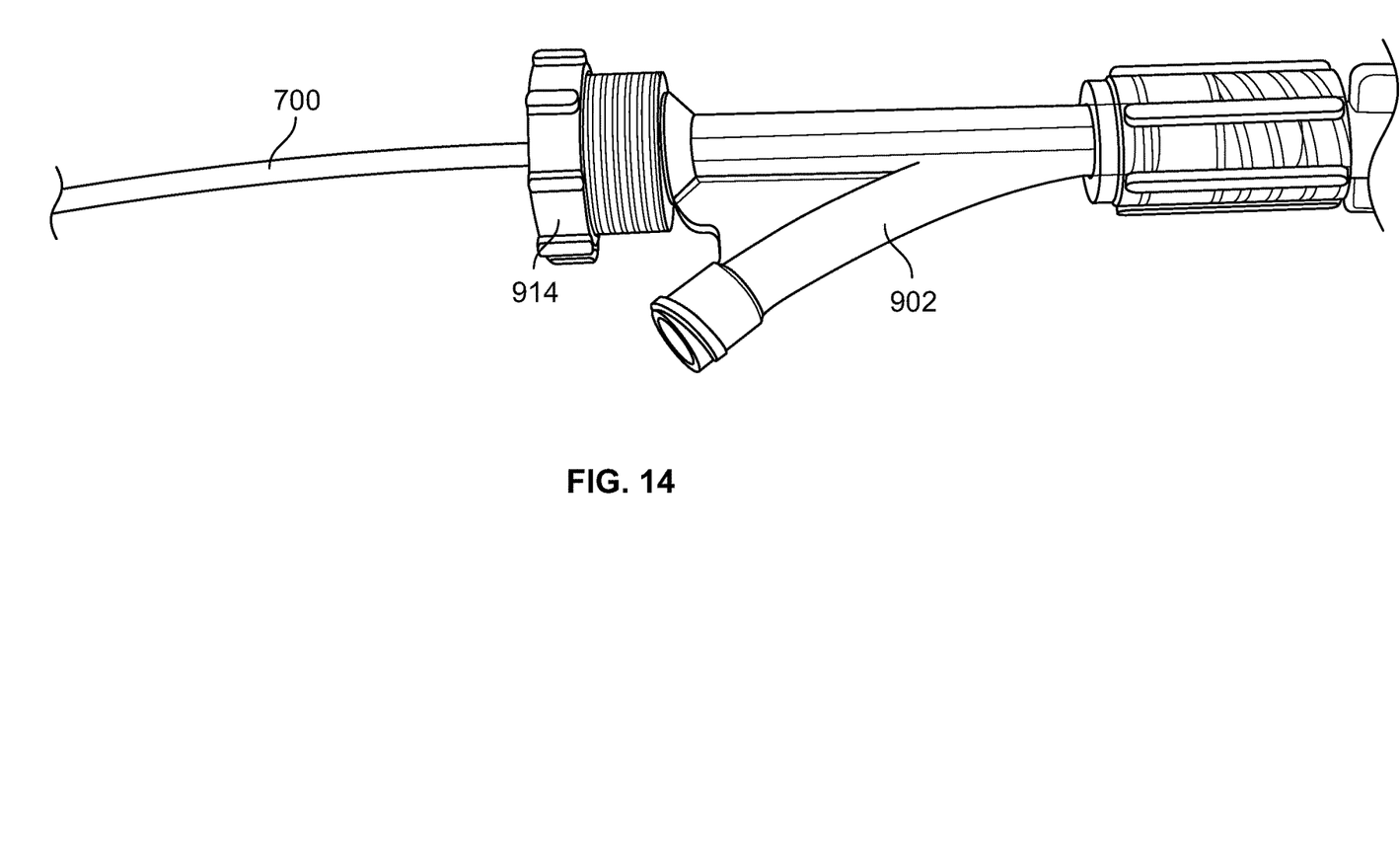
FIG. 14 shows an enlarged view of a portion of the proximal portion of the catheter of FIG. 13.

As shown in FIG. 9, the catheter tube 102 is designed to fit through the biopsy channel of an endoscope positioned within the esophagus to reach a food blockage, but can also be advanced adjacent to an endoscope and can also be advanced orally without the aid of an endoscope. The catheter tube 102 is also bendable and maneuverable as the endoscope bends and maneuvers, yet is rigid enough to withstand kinking.

In this example (see FIGS. 9 and 15), there is a Y-fitting 904 wherein one arm 906 of the Y is attached to and forms the suction port 902, and another arm 908 of the Y accommodates the stylet 700.

Figure 15:
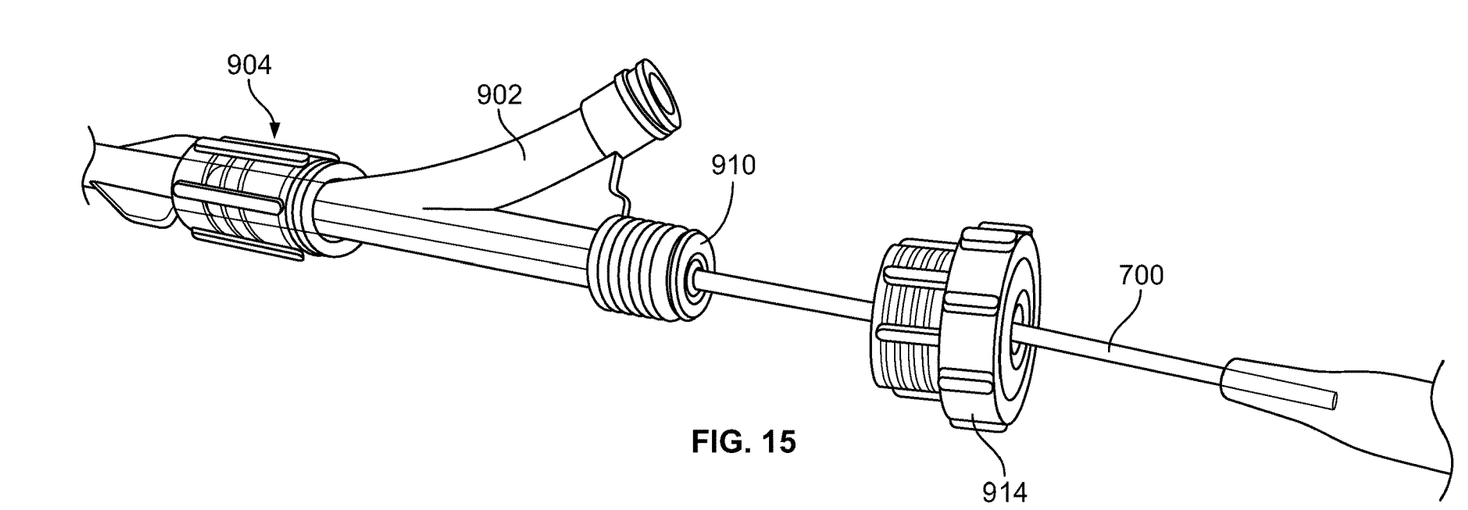
FIG. 15 shows another view of the portion of the proximal portion of the catheter of FIG. 14 with a cap of the suction port removed.
Figure 16:
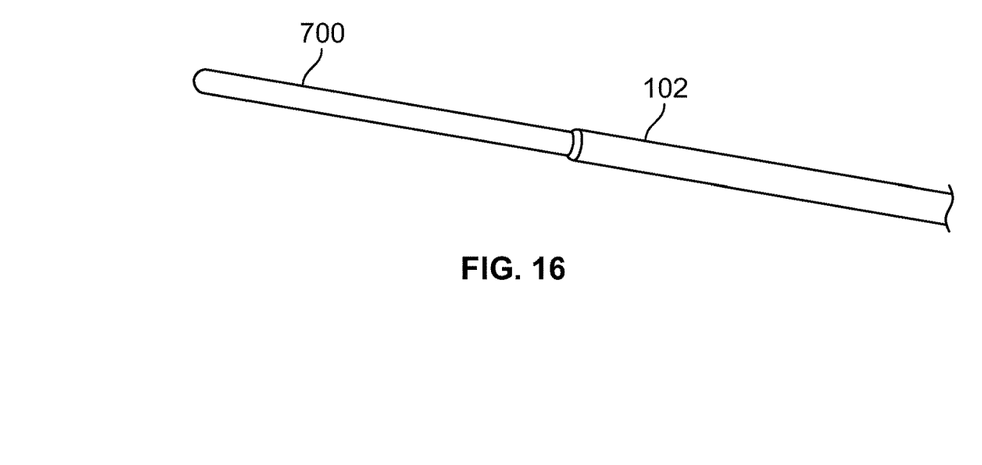
FIG. 16 shows a distal end of the catheter of FIG. 15.
Figure 17:
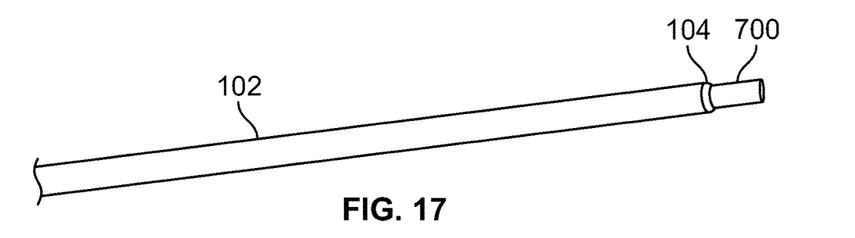
FIG. 17 shows a distal end of the catheter of FIG. 10.

There is also a compression seal 910, or rubber stopper, at the proximal end of the arm 908 that accommodates the stylet 700, so that any air escaping the proximal end is minimized when the stylet 700 is in the catheter tube 102, so that suction and stylet clearance of the vacuum tube can occur simultaneously. When the compression seal 910 is loosened, the stylet 700 can be easily advanced into and out of the catheter tube 102 using a handle 912 of the stylet 700. The compression seal 910 can also secure the stylet 700 in any location along the shaft of the catheter tube 102.

In this example, a cap 914 is threaded onto the proximal end 916 of the arm 908 to retain the compression seal 910 in place. Upon removal of the stylet 700 from the catheter tube 102, the compression seal 910 is configured, in some embodiments, to close the proximal end 916 so that suction can be performed through the catheter tube 102 and the suction port 902.

In the example shown, the catheter tube 102 can work with the stylet 700 completely removed; the stylet 700 can also be introduced as needed, and advanced any distance in the catheter tube 102.

As with previous embodiments, the distal end 104 of the catheter tube 102 can disrupt food, core food, shave food and suction food. The catheter tube 102 wall could be thin and rigid to better accommodate a larger lumen of the tube. The stylet 700 can help support the catheter tube 102 to help prevent kinking if necessary. Thus the stylet 700 can both help clear the suction tube and act as a stylet to stiffen the catheter tube 102.

Figure 18:
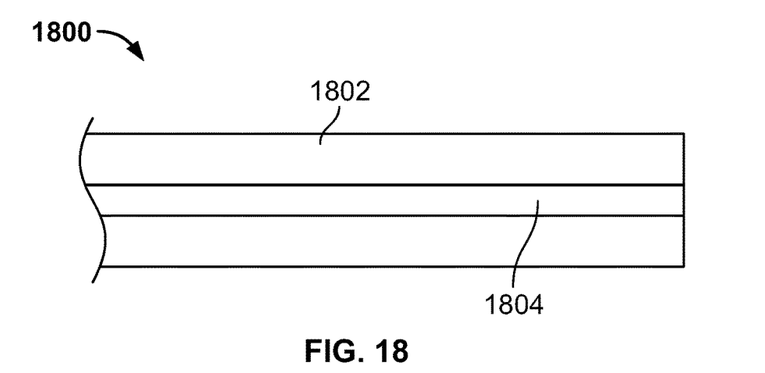
FIG. 18 shows another example embodiment of a stylet for removing a bolus of food or other debris lodged within an esophagus.
Figure 19:
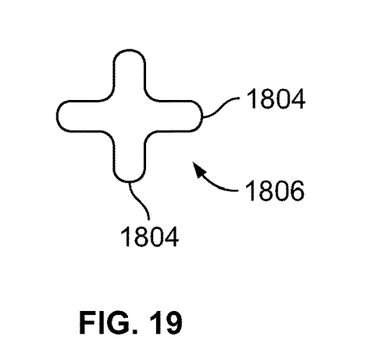
FIG. 19 shows an end portion of the stylet of FIG. 18.

Many alternative designs are possible. For example, in another design shown in FIGS. 18-19, a stylet 1800 could have a spline shape 1802 with splines 1804 formed along the stylet to better accommodate suction when the stylet in is the catheter tube. In other words, spaces 1806 are formed between the splines 1804 to allow suction to be provided through the catheter tube 102 even with the stylet 1800 in place within the catheter tube 102. Other configurations are possible.

Figure 20:
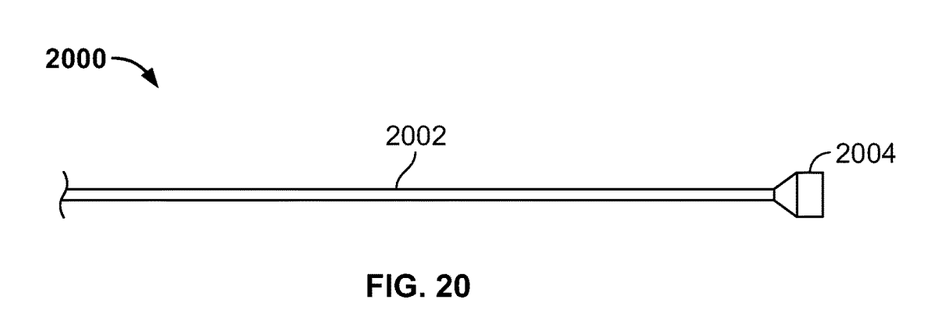
FIG. 20 shows another example embodiment of a system for removing a bolus of food or other debris lodged within an esophagus.
Figure 21:
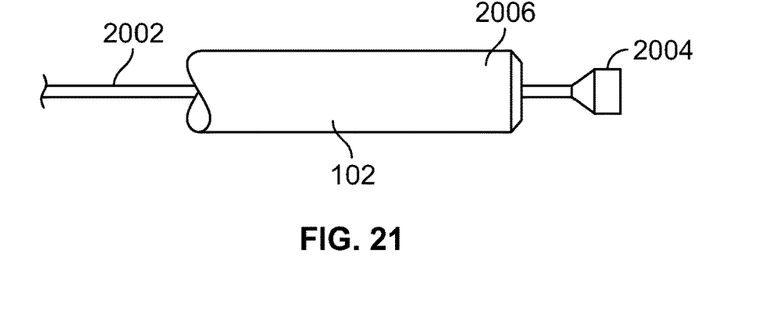
FIG. 21 shows a portion of the device of FIG. 20.

Referring now to FIGS. 20-21, another example of a stylet 2000 is shown. In this example, the stylet 2000 is a wire 2002 with a piston 2004 positioned at an end 2006 thereof. The piston 2004 can be automatically (and/or manually) actuated intermittently or at regularly intervals (such as by a motor) to drive the stylet 2000 through the catheter tube 102 to engage the blockage in the esophagus. Other configurations are possible.

Figure 22:
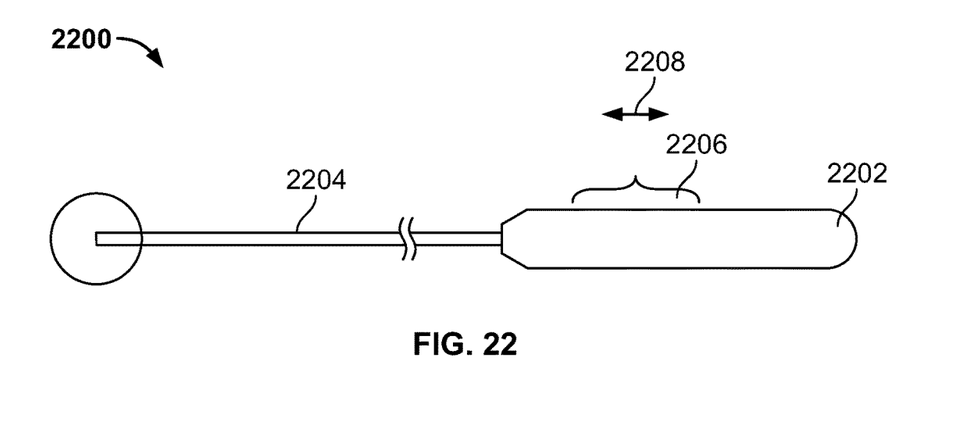
FIG. 22 shows another example embodiment of a system for removing a bolus of food or other debris lodged within an esophagus.
Figure 23:
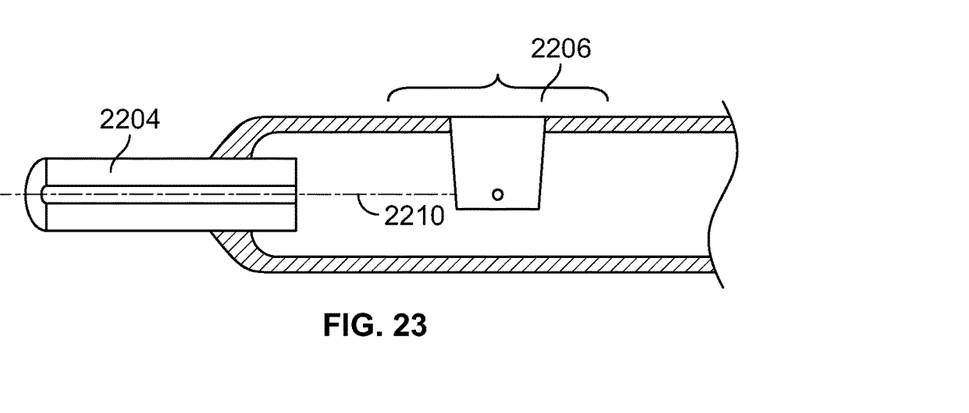
FIG. 23 shows a cross-sectional view of a portion of the device of FIG. 22.
Figure 24:
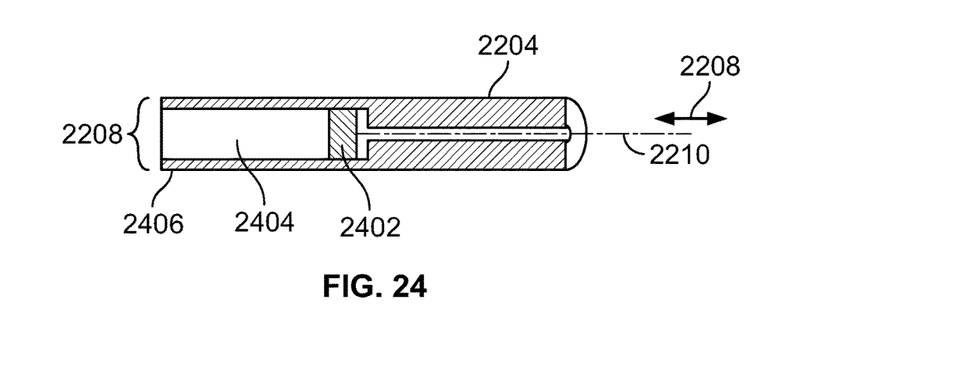
FIG. 24 shows another cross-sectional view of a portion of the device of FIG. 22.

Referring now to FIGS. 22-24, another example device 2200 is shown. The device 2200 is similar to the embodiment of FIGS. 20-21, except that the device 2200 does not necessarily need suction. Instead, the device 2200 includes a handle 2202 and a tube 2204. The handle 2202 includes an actuator member 2206 that can be moved (e.g., by the caregiver's finger or thumb) in a direction 2208 in or out.

The actuator member 2206 is coupled to a wire 2210 that runs through the tube 2204 to an ejector piston 2402. The ejector piston 2402 is positioned within a cavity 2404 formed in a distal end 2406 of the tube 2204. The distal end 2406 of the tube 2204 forms an opening 2408 sized to core or otherwise carve the obstruction as the caregiver moves the handle 2202 and the tube 2204 attached thereto. This is accomplished, for example, by the pieces of the obstruction being carved by the distal end 2406 of the tube 2204 and received in the cavity 2404.

As the cavity 2404 is filled, the caregiver can move the actuator member 2206 to cause the ejector piston 2402 to be moved by the wire 2210 through the cavity 2404 towards the distal end 2406 of the tube 2204 to eject food out of the opening 2408. This process can be done multiple times until the obstruction is cleared. The actuator member 2206 can be biased to return to the retracted position and/or simply be moved in the opposite direction 2208 by the caregiver's finger to return the ejector piston 2402 to the retracted position In some examples, the distal end 2406 of the tube 2204 can be configured to more easily core the obstruction. For example, the distal end can be thinned or serrated so as to be sharper. In other examples, additional features, such as a stainless steel tip, can be added to the distal end 2406 of this (or any other embodiment disclosed herein) to enhance the coring impact of the device 2200.

In some examples, the inner surface of the tubes can be configured to more easily allow cores of the obstruction to pass therethrough. For example, the inner surface of a tube can be coated with a low friction or lubricious material to encourage passage and discourage clumping of the cores. Examples of such low friction materials include, without limitation, Poly vinyl pyrolidone and Hyaluronic acid. Such materials can be typically bonded using heat or ultraviolet light. The external surface of the catheter 102 can optionally also be coated with low friction materials to enable passage through the endoscope. Other mechanisms, such as differing tapers and/or channeling of the inner surface, can also be used.

The examples described above refer to impactions in the esophagus. However, many other similar impactions can be addressed using the systems and methods described herein.

For example, a person can choke while eating, and food can get aspirated and lodge in the trachea, or can also lodge in the lung, specifically any portion of the bronchial tree. Mucus can also become trapped anywhere in the bronchial tree, causing mucus plugging. When this occurs, one or more of the embodiments described herein can be used to core and suction said food or mucus, by placing the device through the working channel of a flexible or rigid bronchoscope as opposed to an endoscope.

One or more of the embodiments described herein can also be used to core, suction and remove trapped blood or blood clots anywhere in the GI tract, specifically the esophagus, stomach, small intestine or large intestine.

One or more of the embodiments described herein can also be used to core, suction and remove trapped food, blood or blood clots, or mucus or mucus plugs, anywhere in the pulmonary organ system, i.e., the trachea or lung i.e. anywhere in the bronchial tree.

One or more of the embodiments described herein can also be used to core and remove blood or blood clots, or atheroma or atheromatous plaque anywhere in the vasculature system, i.e. great arteries or veins, or peripheral vasculature i.e. the peripheral arteries or veins. To core harder materials such as calcified plaque, a stainless steel tip and be attached to the end of the suction catheter.

One or more of the embodiments described herein can also be used to core and remove blood or blood clots, or atheroma or atheromatous plaque anywhere in the heart or coronary arteries. To core harder materials such as calcified plaque, a stainless steel tip can be attached to the end of the suction catheter.

In another example, One or more of the embodiments described herein can be used to core and suction kidney stones from the urinary system, specifically the ureters, bladder and kidneys. To core harder materials such as calcified, struvite, oxalate or uric acid kidney stones a stainless steel tip can be attached to the end of the suction catheter.

In yet another example, one or more of the embodiments described herein can be used to core and remove gallstones or tumors lodged in the biliary tree (common bile duct or peripheral ducts). Harder materials can be cored by attaching a stainless steel tip to the end of the suction catheter.

Although various embodiments are described herein, the embodiments are only examples and should not be construed as limiting.

What is claimed is:

1. A method of clearing a bolus of food within the esophagus of a patient, the method comprising:
   introducing a device into the esophagus to a site of the bolus of food, the device comprising a distal end configured to core the bolus of food, a proximal end, and a tube that comprises a hollow interior;
   coring from the bolus of food a piece that is sized to pass through the hollow interior of the tube using the distal end of the device; and
   applying suction to the proximal end of the device to pass the piece through the hollow interior of the tube and out of the device through the proximal end.

2. The method of claim 1, further comprising introducing an endoscope into the esophagus to the site of the bolus of food, the endoscope defining a channel,
   wherein said introducing the device into the esophagus comprises delivering the device through the channel of the endoscope.

3. The method of claim 2, further comprising visualizing the site of the bolus of food.

4. The method of claim 3, wherein said applying suction to the proximal end of the device to pass the piece through the hollow interior of the tube and out of the device through the proximal end preserves visualization of the bolus of food.

5. The method of claim 2, wherein said introducing the device into the esophagus further comprises deploying the device past a distal end of the endoscope into contact with the bolus of food.

6. The method of claim 2, further comprising maintaining the endoscope in place within the esophagus during said coring from the bolus of food and during said applying suction to the proximal end of the device.

7. The method of claim 2, further comprising:
   repeating the steps of coring and applying suction to reduce a volume of the bolus of food by an amount sufficient to permit the esophagus to naturally pass the bolus of food; and
   after said reducing the volume of the bolus of food, permitting the esophagus to naturally pass the bolus of food into the stomach of the patient.

8. The method of claim 1, wherein the tube comprises both the distal end and the proximal end of the device.

9. The method of claim 1, further comprising using the distal end of the device to repetitively core pieces from the bolus of food, wherein said applying suction to the proximal end of the device further passes the pieces through the hollow interior of the tube and out of the device through the proximal end.

10. The method of claim 1, further comprising:
    repeating the steps of coring and applying suction to reduce a volume of the bolus of food by an amount sufficient to permit the esophagus to naturally pass the bolus of food; and
    after said reducing the volume of the bolus of food, permitting the esophagus to naturally pass the bolus of food into the stomach of the patient.

11. The method of claim 1, further comprising coupling the proximal end of the device to a collection cannister and a source of suction.

12. The method of claim 11, further comprising collecting the piece in the collection cannister.

13. A method of clearing a blockage within the body of a patient, the method comprising:
    introducing an endoscope into the patient to a site of the blockage, the endoscope defining a channel;
    deploying a device through the channel of the endoscope to the site of the blockage, the device comprising a distal end configured to core the blockage, a proximal end, and a tube that comprises a hollow interior;
    coring from the blockage a piece that is sized to pass through the hollow interior of the tube using the distal end of the device; and
    applying suction to the device to pass the piece through the hollow interior of the tube and to move the piece out of the device,
    wherein the blockage comprises a bolus of food impacted within the esophagus of the patient, the method further comprising:
    repeating the steps of coring and applying suction to reduce a volume of the bolus of food by an amount sufficient to permit the esophagus to naturally pass the bolus of food; and
    after said reducing the volume of the bolus of food, permitting the esophagus to naturally pass the bolus of food into the stomach of the patient.

14. The method of claim 13, further comprising coupling the proximal end of the device to a source of suction, and wherein said applying suction to the device comprises applying suction to the proximal end of the device.

15. The method of claim 13, wherein the tube comprises both the distal end and the proximal end of the device.

16. The method of claim 13, wherein said repeating the steps of coring and applying suction to reduce a volume of the bolus of food comprises coring multiple pieces from the blockage and passing the multiple pieces through the hollow interior of the tube and out of the device.

17. The method of claim 13, further comprising coupling the device to a collection cannister and a source of suction.

18. The method of claim 17, further comprising collecting the piece in the collection cannister.

19. The method of claim 13, further comprising visualizing the site of the blockage.

20. The method of claim 19, wherein said applying suction to the device to pass the piece through the hollow interior of the tube and to move the piece out of the device preserves visualization of the blockage.

21. The method of claim 13, wherein said deploying the device further comprises moving the device past a distal end of the endoscope into contact with the blockage.

22. The method of claim 13, further comprising maintaining the endoscope in place within the patient during said coring from the blockage and during said applying suction to the device.

* * * * *